United States Patent
Barbera-Guillem et al.

(10) Patent No.: US 6,749,750 B2
(45) Date of Patent: Jun. 15, 2004

(54) MAGNETIC SHEET ASSEMBLY FOR MAGNETIC SEPARATION

(75) Inventors: Emilio Barbera-Guillem, Powell, OH (US); Marlin O. Thurston, Columbus, OH (US)

(73) Assignee: Biocrystal Ltd., Westerville, OH (US)

( * ) Notice: Subject to any disclaimer, the term of this patent is extended or adjusted under 35 U.S.C. 154(b) by 327 days.

(21) Appl. No.: 09/975,889

(22) Filed: Oct. 11, 2001

(65) Prior Publication Data

US 2002/0084880 A1 Jul. 4, 2002

Related U.S. Application Data

(63) Continuation-in-part of application No. 09/723,008, filed on Nov. 27, 2000, now abandoned.

(51) Int. Cl.$^7$ .......................... B01D 35/06; B03C 1/00; C12N 13/00
(52) U.S. Cl. ................. 210/222; 210/223; 436/526; 435/173.1; 428/40.1; 428/354; 428/692; 428/900; 335/303
(58) Field of Search ................. 210/222, 223, 210/695; 436/526; 435/173.1; 428/40.1, 353, 354, 692, 900; 335/303

(56) References Cited

U.S. PATENT DOCUMENTS

| | | | |
|---|---|---|---|
| 5,078,871 A | * | 1/1992 | McCready .................. 210/223 |
| 5,304,111 A | | 4/1994 | Mitsuno et al. ................ 600/9 |
| 6,110,380 A | | 10/2000 | Barbera-Guillem ......... 210/695 |
| 6,126,835 A | | 10/2000 | Barbera-Guillem et al. 210/695 |

FOREIGN PATENT DOCUMENTS

WO  WO 00/56870  9/2000

* cited by examiner

Primary Examiner—David A. Reifsnyder
(74) Attorney, Agent, or Firm—Benesch, Friedlander, Coplan & Aronoff, LLP

(57) ABSTRACT

A magnetic sheet assembly for application to a device adapted for magnetic separation, the magnetic sheet assembly comprising: a magnetic sheet; a permanent, pressure sensitive adhesive; a carrier sheet; and a non-permanent pressure sensitive adhesive. Also provided is a method of mounting and removably adhering the magnetic sheet assembly to a surface of a device for magnetic separation, the method comprising the steps of aligning the magnetic sheet assembly with the surface of the device; and pressing the aligned magnetic sheet assembly in placing its non-permanent adhesive face into adhesive contact with the surface of the device.

38 Claims, 5 Drawing Sheets

MAGNETIC SHEET ASSEMBLY FOR MAGNETIC SEPARATION

This is a continuation-in-part application of Application Ser. No. 09/723,008 filed Nov. 27, 2000 now abandoned the disclosure of which is substantially incorporated by reference.

FIELD OF THE INVENTION

The present invention relates to a magnetic sheet assembly that can be used in an application of magnetic separation; and more particularly to a magnetic sheet assembly which may be removably held in intimate contact by adhesion to the surface of a device used for magnetic separation of biological molecules or cells.

BACKGROUND OF THE INVENTION

Magnetic separation techniques typically involve the application of a magnetic field to separate ferromagnetic particles contained within a fluid medium. Such techniques use devices that can be divided into two general types: an internal apparatus, or an external apparatus. In the internal apparatus, the ferromagnetic collection structure is contained within the fluid medium in order to intensify the applied magnetic field and improve the resultant gradient. One example of an internal apparatus involves packing steel wool or wires ("collection structures") into a column, wherein the column is situated adjacent to a magnet. A magnetic field is applied to the steel wires such that magnetic particles introduced into the column are attracted toward, and bind to, the steel wires. Another example of an internal apparatus involves loops of ferromagnetic wire that are inserted into a fluid medium. Drawbacks of such systems include entrapment of non-magnetic components; the potential for magnetic shielding of the collection structure therein; breakage of the collection structure during use and/or cleaning; and the requirement for cleaning or disposal of the collection structure between samples. In the external apparatus, generally the magnetic means is situated entirely externally with respect to the separation chamber. Typically, an external apparatus involves a plurality of magnets, or complex magnetic circuitry, placed around the periphery of the separation chamber; wherein the plurality of magnets, or the magnetic circuitry, produces a magnetic field gradient used to effect the magnetic separation. Drawbacks of the external systems include the need for intervention by the user to redesign the placement, positioning, or sizing of the plurality of magnets or circuitry to apply a magnetic field gradient to separation chambers of different sizes; and the additional need for manipulating multiple structures required for placement and positioning of the plurality of magnets or magnetic circuitry. Additionally, some systems use high magnetic field strengths (e.g., 3,000 gauss) which have the potential to alter biological functions of cells. A drawback shared by both currently available internal systems and external systems for magnetic separation is that such systems typically do not allow viewing of magnetic beads (e.g., as coupled to cells or molecules) during the-magnetic separation process (e.g., the magnet or electro-magnet or magnetic circuitry prevent the viewing of magnetic beads during the process).

To address the need for a simple-to-use and efficient magnetic separation system, a cell culture device which can also be used for magnetic separation of cells has been disclosed in co-pending U.S. application Ser. No. 09/526,006, which has issued as U.S. Pat. No. 6,455,310 (the disclosure of which is herein incorporated by reference). However, there is a need for a magnetic sheet which can be removably adhered to such a cell culture device to provide efficiency and versatility for magnetic separation of biological cells or molecules contained therein.

Thus, there is a need for a magnetic sheet assembly that can be manufactured, shipped, and stored as a separate unit and which may be used as an accessory for magnetic separation when applied to a cell culture device.

SUMMARY OF THE INVENTION

It is a primary object of the invention to provide a simple, cost effective construction of a magnetic sheet assembly which can be in a non-adherable form, but which can be easily converted into an adherable form when it is desired to removably adhere the magnetic sheet assembly to the surface of a device for magnetic separation.

It is another object of the invention to provide a magnetic sheet assembly that can be easily handled while it is placed in a packing case for shipping to a user site, easily handled while removing it from the packing case, and easily manipulated so as to be removably adhered to the desired surface of a device for magnetic separation.

It is another object of the invention to provide a magnetic sheet assembly which remains non-adherable during packing, storage, and shipping modes, until it is desired to be removably adhered to the surface of a device for magnetic separation.

It is another object of the invention to provide a magnetic sheet, having a magnetic pole spacing and field strength that can maximize magnetic separation.

It is a further object of the present invention to provide a magnetic sheet assembly adapted to permit ready adhesion to and removal from a surface of a device for magnetic separation, while leaving substantially no adhesive residue on the surface so as to avoid impairment of subsequent microscopic analysis in the device of components (e.g., cells) which are a result of magnetic separation.

One of the novelties of the magnetic sheet assembly according to the present invention is that it allows easy fabrication (such as during cutting, packaging, and handling) of a magnetic sheet assembly adapted to permit ready adhesion to and removal from a surface of a device for magnetic separation, as well as being adapted to provide efficient magnetic separation.

These and other objects and advantages of the invention will become more apparent from the following detailed description taken in conjunction with the accompanying drawings.

DETAILED DESCRIPTION OF THE INVENTION

Definitions

The term "device" is used herein, for purposes of the specification and claims, to mean a vessel adapted for magnetic separation of cells (e.g., mammalian cells, animal cells, plant cells, and the like), wherein the vessel comprises a closed environment (e.g., chamber), and wherein it may be desired to perform magnetic separation of cells from a mixed population of cells that may be contained within the vessel. In a preferred embodiment, the device is a cell culture device disclosed in co-pending U.S. application Ser. No. 09/526,006 which has issued as U.S. Pat. No. 6,455,310 and its dependents. Briefly, in this preferred embodiment as relative to use with magnetic separation, the cell culture device is comprised of a frame to which is contacted and secured taut thereto, in a leak-proof sealing arrangement, two liquid impermeable membranes. At least one of the membranes is gas-permeable. Preferably, each membrane comprises a thin polymeric film; and more preferably, the membrane comprises a film of polystyrene or polypropylene having a thickness of from about 0.001 inches to about 0.004 inches. The chamber of the cell culture device, formed by the frame and membranes, is accessed by at least one access port which extends between the outer surface of the frame and the chamber. The at least one access port serves as a means by which substances (e.g., cells in a fluid and/or tissue culture growth medium) can be introduced into, or withdrawn from, the chamber which is maintained as sterile. The at least one access port is sealed by a septum which comprises an elastomeric, gasket material that fills all or a substantial portion of the access port, and which is sufficiently pliable to be self-sealing; e.g., thereby allowing for penetration by a tip, and resealing after tip withdrawal.

Throughout the following description of the invention, various terms are used such as "upper", "lower", "top", "bottom", "first", "second", "inner", "outer", and the like. These terms are words of convenience in order to distinguish between different elements. While such terms are provided to explain the device or elements relative to positions in which they may normally be used, such terms are not intended to be limiting as to how the different elements may be utilized.

As understood in the art, and throughout the following description of the invention, generally the terms "magnetic beads" and "magnetic particles may be used interchangeably in describing their use in a magnetic separation process.

Figure 1:
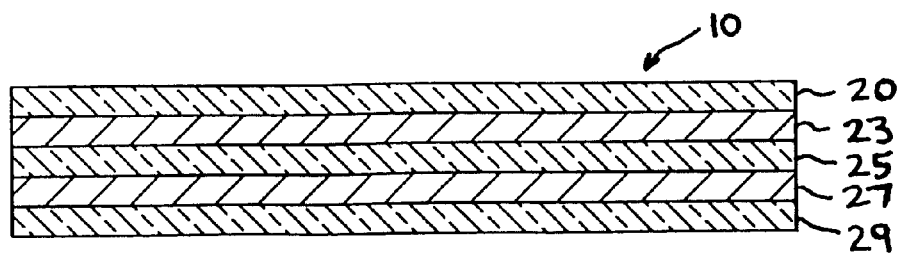
FIG. 1 is a cross sectional side view of one embodiment of a magnetic sheet assembly according to the present invention.
Figure 2:
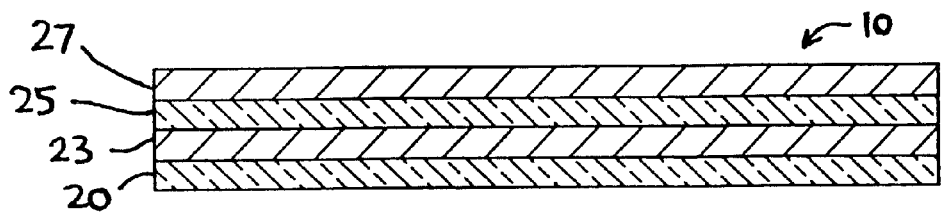
FIG. 2 is a cross sectional side view of another embodiment of a magnetic sheet assembly according to the present invention.
Figure 3:
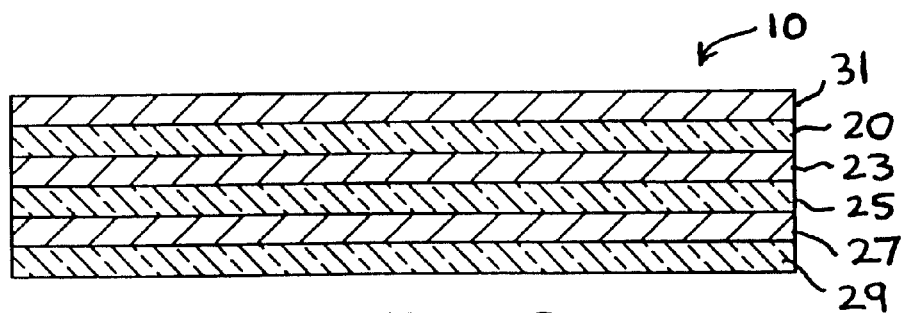
FIG. 3 is a cross sectional side view of another embodiment of a magnetic sheet assembly according to the present invention.
Figure 4:
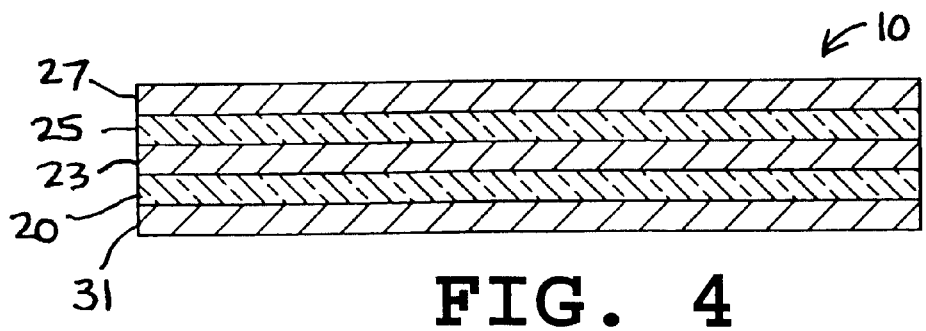
FIG. 4 is a cross sectional side view of another embodiment of a magnetic sheet assembly according to the present invention.

Referring to FIG. 1, a magnetic sheet assembly 10 comprises, in assembled order, a magnetic sheet 20, a permanent adhesive 23, a carrier sheet 25, a non-permanent adhesive 27, and a release liner 29. This illustrated embodiment is particularly useful for providing a magnetic sheet assembly which remains non-adherable during packing, storage, and shipping modes, until it is desired to be removably adhered to the surface of a device for magnetic separation. Referring to FIG. 3, the magnetic sheet assembly 10, as illustrated in FIG. 1, may further comprise a layer 31, wherein layer 31 may be a material selected from the group consisting of a protective coating, a label, and a combination thereof. Referring to FIG. 2, a magnetic sheet assembly 10 comprises, in structural order, a magnetic sheet 20, a permanent adhesive 23, a carrier sheet 25, and a non-permanent adhesive 27. This illustrated embodiment is particular useful for providing a magnetic sheet assembly adapted to permit ready adhesion to and removal from a surface of a device for magnetic separation. Referring to FIG. 4, the magnetic sheet assembly 10, as illustrated in FIG. 2, may further comprise a layer 31, wherein layer 31 may be a material selected from the group consisting of a protective coating, a label, and a combination thereof.

A magnetic sheet 20 comprises at least one substantially flat magnetic sheet having the following characteristics:

(a) a surface magnetic field having a field strength, as measured by a gaussmeter, in a range of from about 250 to about 1500 gauss, and more preferably in a range of from about 450 to about 1200 gauss;

(b) sufficient flexibility to permit the magnetic sheet, as part of an assembly of which the release liner has been removed, to be separated from a device to which it is removably adhered by pulling the magnetic sheet apart from the device (as will be more apparent from the following descriptions and illustrations);

(c) is magnetized with magnetic poles of alternating polarities, which poles being generally arranged as a plurality of parallel, spaced apart lines that are spaced to maximize efficiency of magnetic separation, or may comprise magnetic poles which are positioned to form a combination of a plurality of parallel spaced apart lines and a plurality of perpendicular spaced apart lines in forming a grid pattern for maximizing efficiency of magnetic separation (as will be more apparent from the following descriptions and illustrations); and (d) is generally dimensionally coextensive with the surface to which the magnetic sheet assembly (without the release liner) is to be removably adhered.

A magnetic sheet may include, but is not limited to, a sheet consisting of a fine magnetic powder such as barium ferrite loaded into a thermoplastic binder; a sheet of plastics or vinyl material impregnated with a ferromagnetic material; a sheet of synthetic resin material having mixed therein a magnetic powder; magnetic particles embedded in a polymer sheet of typically 0.7 mm or 0.030 inches thickness; a vinyl material including magnetic materials dispersed therethrough; a fibrous or non-fibrous material having bonded thereto a plurality of magnets, as will be described herein in more detail; or other suitable material having properties compatible with its intended purpose. In a preferred embodiment, the magnetic sheet is comprised of a flexible barium ferrite magnet material, or a flexible strontium ferrite magnet material, or a neodymium iron boron bonded magnetic material, or a combination thereof. Suitable commercially available magnetic sheets may include, but are not limited to a strontium ferrite-based material available under the trademark "PROMAG", or available under the trademark "PLASTALLOY 6". As apparent to those skilled in the art, the thickness of the magnetic sheet will vary depending on factors which include, but are not limited to, the composition of the magnetic sheet material, whether the magnetic sheet comprises one or more sheets, the desired field strength, and the spacing of the magnetic poles. In that regard, and for purposes of illustration but not limitation, the thickness of the magnetic sheet may range from about 0.2 mm to about 5 mm. A preferred thickness of a suitable commercially available, flexible strontium ferrite-based material of from about 450 Gauss to about 1000 Gauss is in a range of from about 0.03 to about 0.06 inches. In a preferred embodiment, the magnetic sheet is generally be dimensionally coextensive in length, width, and shape with the surface to which it is desired to be detachably secured.

In a preferred embodiment, permanent adhesive 23, carrier sheet 25, and non-permanent adhesive 27 together comprise a double-sided, pressure sensitive, adhesive laminate. Preferably, the double-sided, pressure sensitive, adhesive laminate (and the adhesive properties associated therewith) is stable over a broad range of temperatures, particularly a range of from at least 4° C. to at least 50° C. The carrier sheet of the laminate may be selected from a variety of carrier sheet materials suitable for use in pressure-sensitive adhesive products. The carrier sheet is generally thin and flexible, and preferably the carrier sheet has a thickness in the range of from about 0.03 mm to about 0.25 mm; and more preferably, the carrier sheet has a thickness of about 0.002 inches. The carrier sheet material may be fibrous, non-fibrous, or a combination thereof. The carrier sheet may be a suitable polymeric film, fabric (e.g., nylon), paper, cellulose, and the like. In a preferred embodiment, the carrier sheet may comprise a polymer or copolymer including, but not limited to, a polystyrene, an acrylic polymer (e.g., polymethylmethacrylate), a vinyl polymer (e.g., vinyl chloride or ester, plasticized vinyl polymer, and the like), a polycarbonate, a polyolefin, a polyester, a cellulose acetate. In a more preferred embodiment, the carrier sheet comprises a polyester. The carrier sheet may further comprise any conventional stabilizers, plasticizers, or fillers, and the like that may be needed to further provide optimum characteristics, e.g., for flexibility, tensile strength, suitability for being coated on one side with a permanent adhesive and the opposite side with a non-permanent adhesive. Ideally, the carrier sheet should not be negatively affected by (in terms of its intended purpose), nor negatively affect (in terms of their intended purpose) the adhesive layers thereon.

A "permanent adhesive" has a well known, art recognized meaning to describe an adhesive which forms a strong bond with a substrate to which it is applied, so that neither the adhesive nor a carrier sheet to which it is applied can be removed without damaging it or the substrate. More specifically, the permanent adhesive is provided to fixedly bond the magnetic sheet to the pressure sensitive adhesive laminate. Typically, permanent adhesives are described as having a peel force in the order of 3 pounds or more. "Pressure sensitive" has a well known, art recognized meaning to describe an adhesive which quickly bonds when contact pressure is applied to force the adhesive to contact the substrate; e.g., sufficient tack to adhere to a substrate using only light pressure, such as the amount of pressure administered with a hand. Conventional pressure sensitive permanent adhesives are well known in the art, and are commercially available from adhesive manufacturers. For example, one family of pressure sensitive permanent adhesives includes acrylic base adhesives. Illustrative examples include, but are not limited to, compositions comprised of: a polymer backbone such as an acrylic or methylacrylic and a polymerizable monomer such as styrene or alpha-methylstyrene; an acrylic ester and a polymer acrylic monomer; or one or more acrylic esters of an alcohol and a polymerizable monomer (e.g., polystyrene, polyethylene, and the like). Another family of pressure sensitive permanent adhesives includes rubber-based adhesives such as a blend of styrene-butadiene rubber and polyisoprene with a suitable conventional tackifier. A preferred pressure sensitive permanent adhesive used on one side of the double-sided, pressure sensitive, adhesive laminate is available under the product designation AS-28B (Adhesives Research, Inc.). In general, the thickness of pressure sensitive permanent adhesive on the adhesive laminate may vary depending on its composition. A typical thickness of the pressure sensitive permanent adhesive may be in a range of from about 0.0003 to about 0.003 inches; and more preferably, is about 0.0005 inches. The pressure sensitive permanent adhesive may be applied to one side of the carrier sheet, in fabricating the double-sided pressure sensitive adhesive laminate, by any conventional method known in the art such as by coating (e.g., brush coating, knife coating, transfer coating, roll coating, and the like), dispersion, spraying, calendaring, and the like.

A "non-permanent adhesive" has a well known, art recognized meaning to describe an adhesive which can be peeled off, together with the carrier sheet to which it is applied, from the substrate without damage to either the non-permanent adhesive or the substrate. Typically, non-permanent adhesives are described as having a peel force of less than about 2 pounds. It is a significant advantage offered by the magnetic sheet assembly of the present invention to be comprised of double-sided, pressure sensitive, adhesive laminate which having applied on one side a pressure sensitive non-permanent adhesive, wherein the non-permanent adhesive enables repeated application and removal of the magnetic sheet assembly (minus the release liner) with respect to the surface of a cell culture device without the deposit of substantially any adhesive residues on the surface of the cell culture device. The non-permanent adhesive face of the adhesive laminate permits readherence of the magnetic sheet assembly to the contact surface of the same or different cell culture device. More specifically, the pressure sensitive non-permanent adhesive is: (a) of sufficient cohesion to keep the magnetic sheet assembly in adhesive contact with the surface of a cell culture device for a prescribed period of time necessary for a magnetic separation process to be initiated and completed (typically a time in a range of from about 10 minutes to about 4 hours); and (b) is of a light to moderate tack to permit the magnetic sheet assembly to be lifted (e.g., peeled) from the cell culture device to which it was in close adhesive contact, wherein the non-permanent adhesive releases clearly from the surface of the cell culture device as the magnetic sheet assembly is removed, so as to avoid impairment of microscopic examination through that surface after the process of magnetic separation is completed. Thus, when the adhesive "releases clearly from" the surface of the device in removal of the magnetic sheet from the cell culture device, there is minimal (less than 5% of the surface covered by the adhesive retains any visible adhesive residue upon removal) to no adhesive residue remaining on the surface. With regard to the latter, a significant advantage of cell culture device disclosed in co-pending U.S. application Ser. No. 09/526,006, which has issued as U.S. Pat. No. 6,455,310 (and its dependents) is the quality of the optics when viewing cells, present in the cell culture device, through the membrane (e.g., a gas permeable, liquid impermeable, polymer film) of the device. Thus, it is not desirable to impair the optics by leaving adhesive residue on the surface of the cell culture device. Conventional pressure sensitive non-permanent adhesives, particularly suited for the intended purpose as outlined above, are well known in the art, and are commercially available from adhesive manufacturers. For example, useful synthetic or natural rubber based adhesive compositions may comprise 100 parts elastomeric component (e.g., styrene butadiene rubber, natural rubber, silicone rubbers, isoprene, and the like), about 3 to 30 parts crosslinking resin (e.g., alkyl phenolic resins, aryl phenolic resins, and the like), about 1 to 15 parts accelerator ("catalyst", e.g., zinc salts, acid accelerators (e.g., strong inorganic acids, or oxalic acid), and the like), and about 20 to about 70 parts tackifier (hydrocarbon monomer resins, terpenes, phenols, and the like); and may further comprise other optional components (e.g., conventional additives such as antioxidants, colorants, fillers, plasticizers, and the like). In another example, a useful acrylic based adhesive composition includes, but is not limited to, an acrylic elastomer (100 parts; e.g., a copolymer of isooctyl acrylate and acrylic acid) and a tackifier (10 to 30 parts), and may further comprise one or more additives. Conventional pressure sensitive non-permanent adhesives, having properties particularly suited for the intended purpose as outlined above, are manufactured and available from such sources as Adhesives Research, Inc., 3M Company, Acutek Adhesive Specialties, Dow Corning Corporation, and Avery Dennison Manufacturing Company. A preferred pressure sensitive non-permanent adhesive used on one side of the double-sided, pressure sensitive, adhesive laminate is available under the product designation AS-124 Mod. (Adhesives Research, Inc.). In general, the thickness of pressure sensitive non-permanent adhesive on the adhesive laminate may vary depending on its composition. A typical thickness of the pressure sensitive non-permanent adhesive may be in a range of from about 0.0003 to about 0.003 inches; and more preferably, is about 0.0005 inches. The pressure sensitive non-permanent adhesive may be applied to one side of the carrier sheet, in fabricating the double-sided, pressure sensitive, adhesive laminate, by any conventional method known in the art such as by coating (e.g., brush coating, knife coating, transfer coating, roll coating, and the like), dispersion, spraying, calendaring, and the like.

A release liner is provided to cover the non-permanent adhesive, of the double-sided pressure sensitive adhesive laminate, until it is desired to expose the non-permanent adhesive. Removal of the release liner permits the magnetic sheet assembly to be removably adhered to a surface of a cell culture device. When a part of the magnetic sheet assembly, the release liner protects the non-permanent adhesive surface from collecting lint or dust or a substrate which it is not intended to be adhered. A release liner, as known in the art, has a surface that is not very adherable by the adhesive which it covers, and thus is very releasable from the adhesive. Typical release liners are a paper or polymer film which may be coated with a release coating. Examples of release liner materials include, but are not limited to, paper, polyethylene-coated paper, polyethylene film, polyester film, polyvinyl film, polypropylene film, and the like. Release coatings may include, but are not limited to, a silicon compound such as a silanol-stopped dimethylpolysiloxane, or dimethylvinyl-stopped dimethylpolysiloxane. A desirable thickness of a release liner may range from about 0.001 to about 0.004 inches. A preferred release liner comprises a polyester, of about 0.002 inches thick, coated with a release coating.

In some embodiments, the magnetic sheet assembly may further comprise layer 31 comprising a material selected from the group consisting of a protective coating, a label, and a combination thereof. As apparent to those skilled in the art, a thin protective coating, having a substantially uniform thickness, may be provided to generally improve magnetic properties and/or durability of the magnetic sheet. Various protective coatings for magnets are known in the art to include, but are not limited to, polyurethane, a polyurethane rubber compound, polyester, polyester-imide, polyamide, and the like; and may further comprise a colorant. A label may be provided on the surface of the magnetic sheet which is opposite to the surface of the magnetic sheet which is bound to a permanent adhesive. Preferably, the label is generally dimensionally coextensive with the magnetic sheet to which it is applied. In one preferred embodiment, the label is made of a flexible or semi-flexible material which may include, but is not limited to a vinyl, fabric, or a paper. Preferably, the label is adhered to the magnetic sheet by a permanent adhesive or laminated onto the magnetic sheet; or may comprise printing and coloring directly on the magnetic sheet surface. The label may comprise color, printing, logos, trademarks, product information, instructions for use, advertisements, company contact information, ordering information, and a combination thereof.

EXAMPLE 1

This example illustrates a method of the making the magnetic sheet assembly according to the present invention. A magnetic sheet was selected which comprised a flexible, high energy, strontium ferrite material having a surface magnetic field strength of about 500 gauss. Attached to magnetic sheet was a double-sided, pressure sensitive, adhesive laminate having applied on one side a pressure sensitive permanent adhesive and on the opposite side a pressure sensitive non-permanent adhesive (as previously described herein). Preferred double-sided, pressure sensitive, adhesive laminates comprised a polyester carrier sheet, and a pressure sensitive permanent adhesive/pressure sensitive non-permanent adhesive: AS-28B/AS-124 Mod. (Adhesives Research, Inc), or a high tack acrylic/low tack removable acrylic (Item 0297005; Acutek Adhesive Specialities). The release liner comprised either a release coated paper or a release coated polyester. The magnetic sheet was aligned with the exposed permanent pressure sensitive adhesive side of the double-sided pressure sensitive adhesive laminate, and the magnetic sheet and double-sided pressure sensitive adhesive laminate were pressed together in adhesive contact in permanently bonding together the magnetic sheet and double-sided pressure sensitive adhesive laminate in forming the magnetic sheet assembly. As apparent to one skilled in the art, the magnetic sheet assembly, dimensioned for used with a device for magnetic separation, may be produced in the desired size and shape, or may be formed from larger sheets which then are cut using any conventional means (e.g., die cut) to the desired size and shape.

EXAMPLE 2

This example illustrates methods of using of the magnetic sheet assembly according to the present invention. In one embodiment of a method according to the present invention for mounting and removably adhering a magnetic sheet assembly (comprising a magnetic sheet, a permanent adhesive, a carrier sheet, and a non-permanent adhesive which clearly releases from a substrate upon removal) to a surface of a device for magnetic separation (such as a cell culture device) which comprises the steps of:

1) aligning the magnetic sheet assembly, having an exposed face comprising a non-permanent adhesive, with the surface of the device onto which it is desired to mount the magnetic sheet assembly; and
2) pressing the aligned magnetic sheet assembly in placing the non-permanent adhesive face into adhesive contact with the surface of the device to removably adhere the magnetic sheet assembly to the surface of the device.

Figure 5:
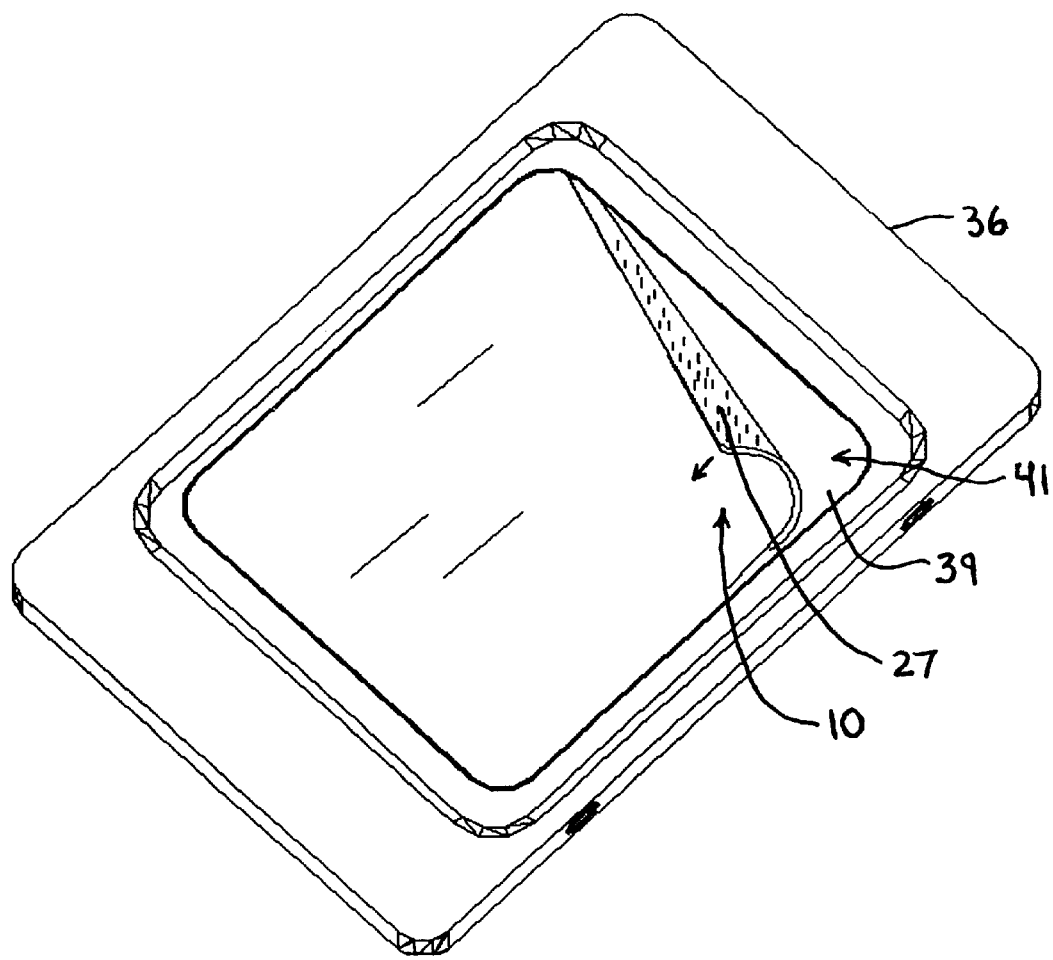
FIG. 5 is top perspective view of an embodiment of a process of removing the magnetic sheet assembly from a cell culture device.

As illustrated in FIG. 5, the method may further comprise the step of removing magnetic sheet assembly 10 from cell culture device 36 by lifting and separating magnetic sheet assembly 10 from cell culture device 36 (and surface 39) to which it was in adhesive contact, wherein during the removal, non-permanent adhesive 27 releases clearly from surface 39 of cell culture device 36. It is noted for FIG. 5, that surface 39 is one of two surfaces that form opposing sides of chamber 41 of cell culture device 36. Additionally, a preferred shape and size of the magnetic sheet assembly, to be dimensionally coextensive with surface 39 as illustrated in use in FIG. 5, is a length of about 8.25 cm, and a width of about 7 cm (e.g., in covering surface 39 of about 7.5 cm by about 6.5 cm).

In another embodiment of a method according to the present invention for mounting and removably adhering a magnetic sheet assembly (comprising a magnetic sheet, a permanent adhesive, a carrier sheet, a non-permanent adhesive which clearly releases from a substrate upon removal, and a release liner) to a surface of a device for magnetic separation (e.g., a cell culture device) which comprises the steps of:

1) removing the release liner from the magnetic sheet assembly so as to expose a face of the magnetic sheet assembly comprising the non-permanent adhesive;
2) aligning the magnetic sheet assembly, having an exposed face comprising a non-permanent adhesive, with the surface of the device onto which it is desired to mount the magnetic sheet assembly; and
3) pressing the aligned magnetic sheet assembly in placing the non-permanent adhesive face into adhesive contact with the surface of the device to removably adhere the magnetic sheet assembly to the surface of the device.

As illustrated in FIG. 5, the method may further comprise the step of removing the magnetic sheet assembly from the cell culture device by lifting and separating the magnetic sheet assembly from the cell culture device to which it was in adhesive contact, wherein during the removal, the non-permanent adhesive releases clearly from the surface of the cell culture device.

In either embodiment, the magnetic sheet assembly, by virtue of the exposed non-permanent adhesive face, may be reapplied by the user to a surface of one or, successively, more devices as many as several (e.g., 5) or more additional times. In that regard, the magnetic sheet assembly will readhere each time it is manually pressed onto the aligned contact surface, which may be the same surface of a device to which it was previously applied or which may be an entirely new surface (e.g., a different surface of the same device, or a surface of a different device).

EXAMPLE 3

This example illustrates some preferred magnetization patterns and magnetic pole spacing which have been found experimentally to have the unexpected result of significantly increasing the efficiency of magnetic separation of magnetic beads complexed to a substance (e.g., molecule such as, but not limited to, a protein, nucleic acid molecule, drug, and the like; or biological cells including, but not limited to, eukaryotic cells) desired to be separated. For ease of description, magnetic beads or magnetic particles complexed to a substance is referred to herein as "magnetic bead complexes". The magnetic sheet assemblies illustrated in this example were produced according to Example 1. In assessing different magnetization patterns, there are several considerations. For purposes of the invention, the magnetization pattern of the magnetic sheet is provided for generating magnetic flux across the face of the magnetic sheet that is placed adjacent to the surface of a device. The pull force (the magnetic force to attract and hold magnetic bead complexes along the inner surface of the adjacent device) of the magnetic sheet will have to be sufficient to be effective for magnetic separation over the distance between the surface of the magnetic sheet and the inner surface of the device to which the magnetic sheet assembly is removably adhered. The pull force of a magnetic sheet, with respect to distance therefrom, will be a function of parameters which include, but are not limited to, the composition of the magnetic sheet, the number of magnetic poles, magnitude of magnetic flux density produced by a pole, spacing of the poles, and arrangement of the poles. For example, while wider pole spacing tends to provide a greater depth (e.g., force over a distance) in magnetic field strength, the gradients of the magnetic field are reduced, as compared to narrower pole spacing. Also, the number of field lines along which magnetic bead complexes may accumulate is reduced. Hence, the overall magnetic effect may be relatively inefficient, with respect to magnetic separation, if pole spacing is too wide. However, narrow pole spacing tends to create a more shallow magnetic field which can minimize the range of working distance with respect to magnetic separation; i.e., the spacing may be so close as to reduce the pull force of the magnetic sheet to be relatively inefficient for magnetic separation in view of the distance between the face of the magnetic sheet and space between the surfaces of an adjacent device.

In magnetic separation of a biological substance (cells or molecules), very small magnetic beads are used for labeling the substance. The magnetic beads act as if they were small bar magnets with a north and south pole separated by a few nanometers. The dipole moment of such a bead is the product of the strength of an equivalent pole and the distance between the poles. When the bead is in a uniform applied magnetic field, the north pole will experience an equal force but in the opposite direction to that experienced by the south pole. The bead will align itself with the field, but the bead may not move, despite how strong the field may be. The fundamental point is that the strength of the applied field at the north pole is desirably different from the field strength at the south pole to facilitate the movement of the bead. In other words, there must be a gradient in the magnitude of the applied magnetic field in order for the bead to experience a force. For example, such a gradient is present in a magnet sheet having alternating parallel north and south poles.

Figure 6:
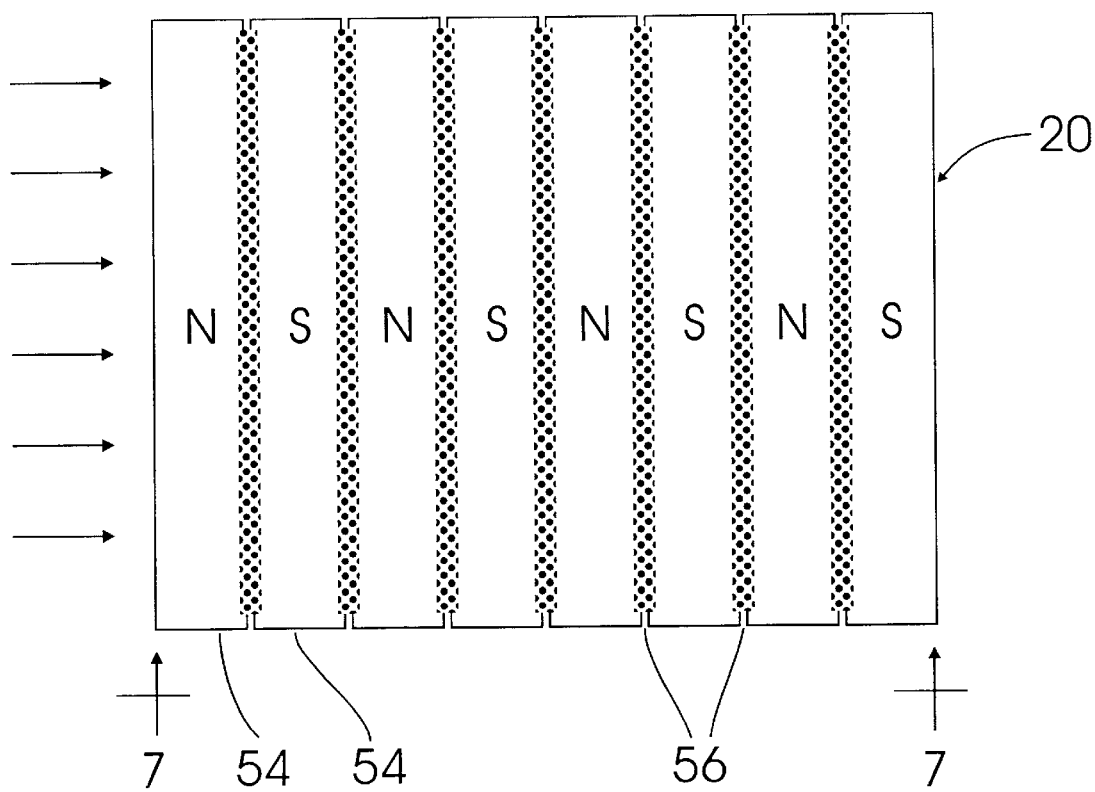
FIG. 6 illustrates a top plan view of one embodiment of a pattern of magnetic polarity of a magnetic sheet for efficient magnetic separation.
Figure 8A:
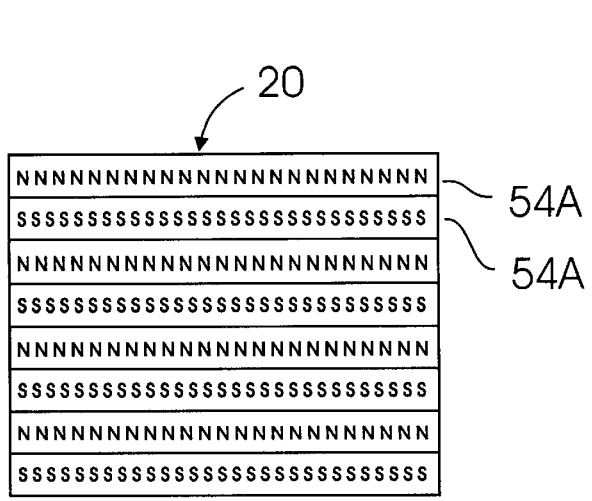
FIG. 8A illustrates a top plan view of another embodiment of a pattern of magnetic polarity of a magnetic sheet for efficient magnetic separation.
Figure 8B:
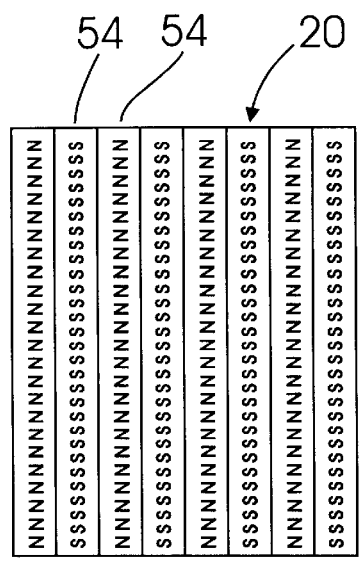
FIG. 8B is a top plan view of a magnetic sheet of a pattern of magnetic polarity that may be combined with the pattern illustrated in FIG. 8A to obtain the pattern of the magnetic sheet illustrated in FIG. 8C.

In one embodiment, and as illustrated in FIGS. 6, 8A, and 8B, the magnetic sheet 20 comprises a plurality of poles of alternating polarities, being generally arranged as a plurality of parallel, spaced apart lines 54. Relative to viewing the magnetic sheet as it lies on a surface, the parallel, spaced apart lines may run along the surface of the magnetic sheet from side to side (e.g. as illustrated in FIG. 8A), or top to bottom (as illustrated in FIGS. 6 & 8B). As shown in FIG. 6, the maximum gradient is along the lines 56 that separate the poles, and hence, is where magnetic bead complexes ("●", FIG. 6) preferably are accumulated. In a process of magnetic separation, various fluids are flowed into and out of the device (e.g., cell culture device previously described herein in more detail). A fluid flow which is parallel to the poles may tend to move some magnetic beads complexes along the lines which the magnetic bead complexes accumulate. While such movement may not be of significant consequence in a magnetic separation process performed in a closed system, in a magnetic separation process it may be preferable to flow a fluid across the lines along which magnetic bead complexes accumulate; i.e., across (perpendicular to) the junctions between north and south poles (see, FIG. 6, wherein arrows represent a preferred fluid flow which is transverse to the poling). Alternatively, it may also be preferred that the magnetic sheet distribute field gradients to trap the magnetic bead complexes with respect to any direction of fluid flow (e.g., a cross poling pattern, as illustrated in FIGS. 8C, and 8D, or a discrete poling pattern, illustrated in FIG. 9A, providing for a pattern of maximum gradients in which magnetic bead complexes tend to accumulate, "●").

Figure 7:
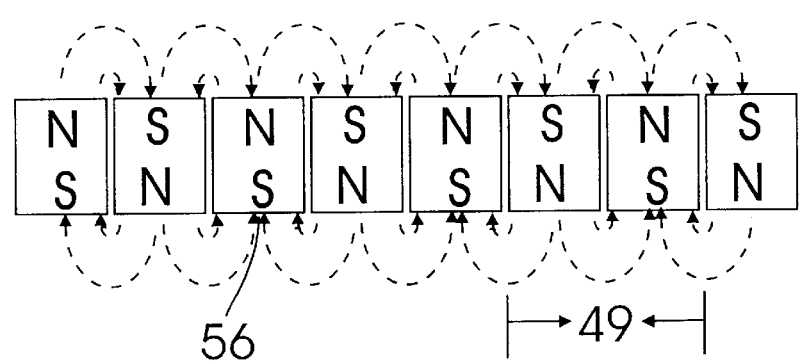
FIG. 7 is a cross-sectional view taken along lines 7—7 of FIG. 6.

Analyzed were a variety of patterns which differ in pole spacing; e.g., about 8 poles per inch (i.e. number of spaced apart lines), about 12 poles per inch, and about 14 poles per inch; wherein the spacing between different poles (e.g., lines formed by the poles) is preferably equidistant. It was determined experimentally that using the magnetic assembly according to the present invention, and in accordance with a preferred embodiment of a magnetic sheet, a spacing of from about 7 to about 12 poles per inch (preferably with equidistant spacing between different pole lines) unexpectedly resulted in maximum efficiency for magnetic separation in considering the distance between the magnetic sheet assembly and the adjoining surface of an adjacent device in which the magnetic separation was performed (e.g., a cell culture device previously described herein). In a preferred pole spacing, and as illustrated in FIG. 7, preferably the distance 49 between a line of north polarity and the next nearest parallel line of north polarity is in a range of from about 3 millimeters to about 0.25 inches; particularly where distance between the magnetic sheet of the magnet sheet assembly and the surface along which the magnetic bead complexes accumulate is in a range of from about 0.002 inches to about 0.004 inches. In that regard, using this preferred pole spacing of from about 7 to about 12 poles per inch in the magnetic sheet assembly according to the present invention, the efficiency was experimentally determined to be at least 5% to 10% greater than wider or narrower pole spacing in a pattern of a plurality of parallel, spaced apart lines.

Figure 8C:
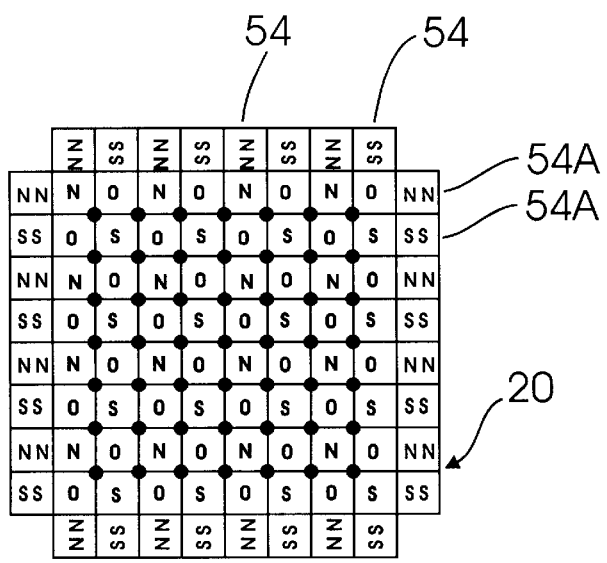
FIG. 8C is a top plan view of an embodiment comprising a magnetic sheet of a pattern of magnetic polarity comprised of doubling poling at right angles.
Figure 8D:
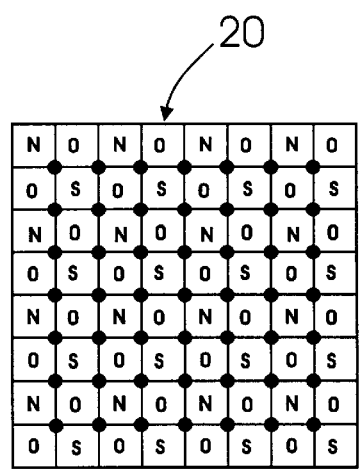
FIG. 8D is a top plan view of another embodiment comprising a magnetic sheet of a pattern of magnetic polarity comprised of doubling poling at right angles.

In another embodiment, and as illustrated in FIGS. 8C and 8D, the magnetic sheet comprises a plurality of poles of alternating polarities, which poles being generally arranged as a plurality of parallel, spaced apart lines 54 (e.g., which run along the planar surface from top to bottom or in a "horizontal" poling pattern, as illustrated in FIG. 8A); and a plurality of poles of alternating polarities, which poles being generally arranged as and a plurality of parallel, spaced apart lines 54A (e.g., which run along the planar surface from side to side or in a "vertical" poling pattern, as illustrated in FIG. 8B) which are perpendicular in respect to, and intersect, lines 54 in forming a grid pattern. Thus, horizontal poling combined with vertical poling can result in a grid pattern in which magnetic bead complexes tend to accumulate at corners in the grid pattern which represent points at which a north pole adjoins with a south pole ("●", FIGS. 8C and 8D). In a preferred embodiment, lines 54 are spaced apart equidistantly, and lines 54A are spaced apart equidistantly. For example, a magnetic sheet comprising a grid pattern (e.g., as illustrated in FIG. 8C) may be formed by combining two magnetic sheets (e.g., combining a magnetic sheet as illustrated in FIG. 8A with a magnetic sheet as illustrated in FIG. 8B, and as held together such as by magnetic forces). Thus, the magnetic sheet assembly may comprise two magnetic sheets which are combined together to form a grid pattern (as illustrated in FIG. 8C). Alternatively, using methods known in the art, a single magnetic sheet may be produced which demonstrates a grid pattern (e.g., double poling at right angles, as illustrated in FIG. 8D). In illustrating a poling pattern comprising double poling at right angles: where two north poles coincide (e.g., are superimposed), the resulting north pole is designated with an "N" (FIGS. 8C and 8D); where two south poles coincide, the resulting south pole is designated with an "S" (FIGS. 8C and 8D); and where a north pole coincides with a south pole, the resulting pole is designated with an "O" (FIGS. 8C and 8D) which is representative of a substantial cancellation of the magnetic field at that point. It was determined experimentally that using the magnetic sheet assembly according to the present invention, and in accordance with a preferred embodiment of a magnetic sheet, with a magnetization pattern comprising a grid of pole lines having spacing of from about 10 poles per inch to about 12 poles per inch (preferably with equidistant spacing between different parallel pole lines) resulted in a significantly increased efficiency (e.g., at least a 10%, or more, greater efficiency) for magnetic separation as compared to patterns comprising poles arranged as a plurality of parallel, spaced apart lines (as illustrated in FIG. 6); and further, unexpectedly resulted in maximum efficiency (at least 5% to 10% greater) for magnetic separation in considering the distance between the magnetic assembly and the surface of an adjacent device when compared to grid patterns of either wider or narrower pole spacings.

Figure 9A:
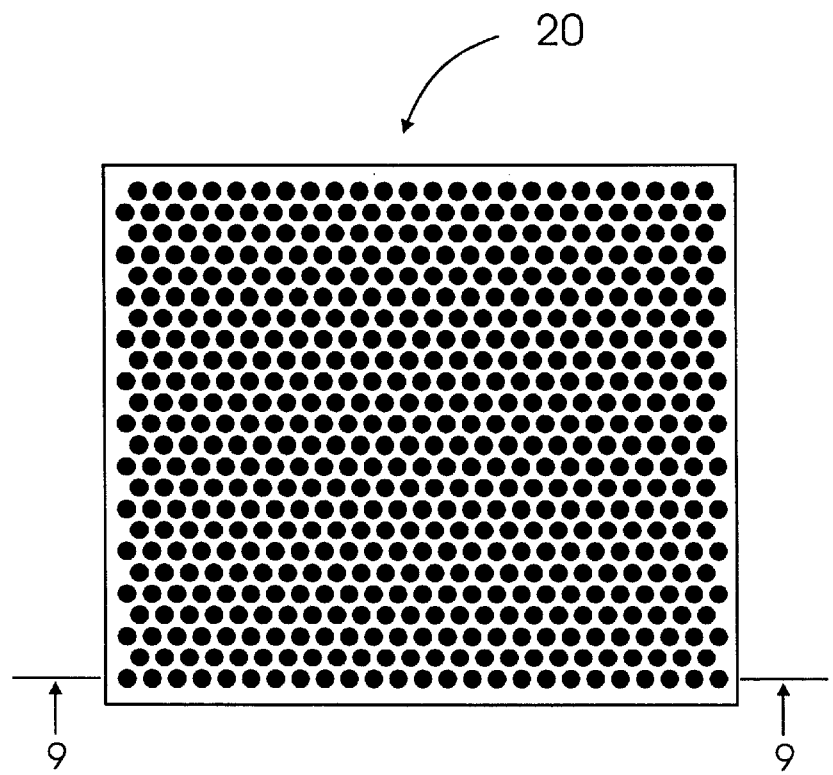
FIG. 9A is a top plan view of another embodiment comprising a magnetic sheet having a poling pattern with a distribution of field gradients that enable trapping of cells irrespective of the directions of fluid flow.
Figure 9B:
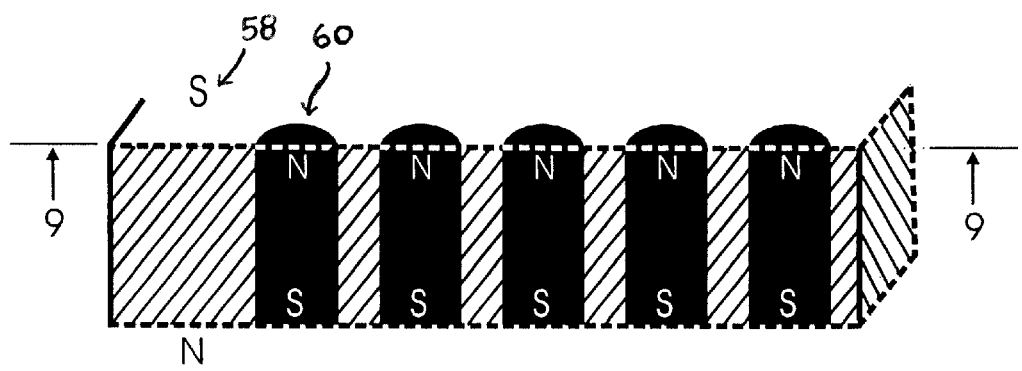
FIG. 9B is a cross-sectional view taken along lines 9—9 of FIG. 9A.

In another embodiment, as illustrated in FIGS. 9A & 9B, magnetic sheet 20 comprises a poling pattern that produces a distribution of field gradients ("●", FIG. 9A) that enable trapping of magnetic bead complexes in any direction of fluid flow along the horizontal plane (planar surface) of the magnetic sheet. To enable this result, it is necessary to avoid long continuous paths of zero gradient; e.g., the zero gradient paths are comprised of small closed loops. For example, in one embodiment as illustrated in FIG. 9B, a magnetic sheet 20 comprises magnetization with a uniform poling in a first poling 58 over substantially all of a planar surface of the magnetic sheet, and a second poling 60 of an opposite polarity to that of first poling 58, wherein the second poling comprises a plurality of spaced apart (an "array") of cylindrical regions which are parallel in relation to first poling 58. Thus, as illustrated in FIGS. 9A & 9B, the magnetic sheet is magnetized with a plurality of south poles on the upper surface (e.g., a face or planar surface) of the magnetic sheet, over which a plurality of north poles (e.g., an array of circular north poles) was then superimposed (using methods known in the art). As a result, the locations of maximum field gradient comprise circular regions around the individual north poles. In use, fluid flow is able to move magnetic bead complexes within the circular regions or along an arc of respective circular regions, but has difficulty in moving magnetic bead complexes from one circular region to another circular region. It is apparent to one skilled in the art that the regions of maximum gradient may comprise a shape other than a circle (e.g., hexagon, square, or the like). However, it is important that each pole be surrounded by an equal area of opposite polarity. An enlarged and cross-sectional view of the poling pattern illustrated in FIG. 9A (taken along line 9—9) is illustrated in FIG. 9B. A preferred shape(s) of the regions of maximum gradient may be used for the present invention to the exclusion shapes other than the preferred shape.

FIG. 9A (independent of reference to FIG. 9B) can also schematically illustrate an embodiment in which the magnet sheet comprises a fibrous or non-fibrous sheet (which may include, but is not limited to, a suitable polymeric film, fabric (e.g., nylon, polyester, and the like), paper, cellulose, and the like) onto one or more planar surfaces of which is bonded a plurality of magnets. The fibrous or non-fibrous sheet comprises a material which is preferably flexible in allowing the magnetic sheet (and the magnetic sheet assembly of which it is a component) to be placed adjacent to, and preferably in contact with substantially all, of a surface of the cell culture device in a method of magnetic separation, particularly where such surface has one or more contours. The plurality of magnets may be bonded to the fibrous or non-fibrous sheet using means known in the art. For example, bonding may include, but is not limited to, an adhesive bond, a bond formed by printing the magnets onto the fibrous or non-fibrous sheet, and the like. It is apparent to one skilled in the art that the magnets (comprising regions of maximum gradient) may comprise a shape such as a circle, or other than a circle (e.g., hexagon, square, or the like). A preferred shape(s) of the regions of maximum gradient may be used for the present invention to the exclusion shapes other than the preferred shape. In view that provided herein have been several embodiments of a magnetic sheet for use in the magnetic sheet assembly according to the present invention, a preferred magnetic sheet may be used for the present invention to the exclusion magnetic sheets other than the preferred magnetic sheet.

In a preferred embodiment of using the magnetic sheet assembly as previously described herein, the magnetic sheet is applied to the membrane surface of the preferred cell culture device. Since the cell culture device typically contains a fluid layer of about two millimeters, magnetic beads used in, and magnetic bead complexes formed during, the magnetic separation process are observable through the opposing membrane surface of the cell culture device. The capability to view magnetic beads and/or magnetic bead complexes during a magnetic separation process is an advantage over the current systems used for magnetic separation.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A magnetic sheet assembly for application to a device adapted for magnetic separation, wherein the magnetic sheet assembly comprises:
    a magnetic sheet;
    a carrier sheet having a first side and a second side;
    a permanent, pressure sensitive adhesive binding the carrier sheet to the magnetic sheet, the permanent pressure sensitive adhesive having a first peel force; and
    a non-permanent, pressure sensitive adhesive applied to the second side of the carrier sheet configured to selectively bind the assembly to the device, the non-permanent, pressure sensitive adhesive having a second peel force less than the first peel force.

2. The magnetic sheet assembly according to claim 1, further comprising a release liner which covers the non-permanent pressure sensitive adhesive.

3. The magnetic sheet assembly according to claim 2, wherein the release liner has a thickness in a range of from about 1 mil to about 4 mil.

4. The magnetic sheet assembly according to claim 2, wherein the release liner has a thickness of about 2 mil.

5. The magnetic sheet assembly according to claim 2, wherein the permanent, pressure sensitive adhesive, carrier sheet, non-permanent pressure sensitive adhesive, and release liner are assembled to form a double-sided, pressure sensitive, adhesive laminate.

6. The magnetic sheet assembly according to claim 1, wherein the magnetic sheet is flexible.

7. The magnetic sheet assembly according to claim 1, wherein the magnetic sheet has a thickness in a range of from about 1 mm to about 2 mm.

8. The magnetic sheet assembly according to claim 1, wherein the magnetic sheet has a surface magnetic field having a field strength in a range of from about 600 to about 1200 gauss.

9. The magnetic sheet assembly according to claim 1, further comprising a layer provided on a surface of the magnetic sheet which is opposite to a surface of the magnetic sheet to which is bound the permanent adhesive; wherein the layer is a material selected from the group consisting of a protective coating, a label, and a combination thereof.

10. The magnetic sheet assembly according to claim 1, wherein the magnetic sheet comprises a plurality of poles of alternating polarities being generally arranged as a plurality of parallel, spaced apart lines.

11. The magnetic sheet assembly according to claim 10, wherein the parallel, spaced apart lines may run along the surface of the magnetic sheet in a direction selected from the group consisting of side to side, and top to bottom.

12. The magnetic sheet assembly according to claim 10, wherein the spacing between the spaced apart lines is equidistant.

13. The magnetic sheet assembly according to claim 12, wherein the spacing is in a range of from spacing about 7 to about 12 poles per inch.

14. The magnetic sheet assembly according to claim 1, wherein the magnetic sheet comprises a magnetization pattern comprising a grid pattern formed by a first plurality of poles of alternating polarities being generally arranged as a plurality of parallel, spaced apart lines which are perpendicular with respect to, and intersect, a second plurality of poles of alternating polarities being generally arranged as a plurality of parallel, spaced apart lines.

15. The magnetic sheet assembly according to claim 14, wherein the spacing between parallel spaced apart lines is equidistant.

16. The magnetic sheet assembly according to claim 15, wherein the spacing of parallel, spaced apart lines is in a range of from spacing about 7 to about 12 poles per inch.

17. The magnetic sheet assembly according to claim 1, wherein the magnetic sheet comprises a magnetization pattern comprising a uniform poling in a first poling over substantially all of a planar surface of the magnetic sheet, and a second poling of an opposite polarity to that of first poling, wherein the second poling comprises a plurality of spaced apart cylindrical regions which are parallel in relation to the first poling.

18. The magnetic sheet assembly according to claim 1, wherein the magnetic sheet comprises a plurality of magnets bonded to a material selected from the group consisting of a fibrous material, and a non-fibrous material.

19. The magnetic sheet assembly according to claim 1, wherein the carrier sheet has a thickness in a range of from about 0.03 mm to about 0.25 mm.

20. The magnetic sheet assembly according to claim 1, wherein the carrier sheet has a thickness of about 2 mil.

21. The magnetic sheet assembly according to claim 1, wherein the pressure sensitive permanent adhesive has a thickness in a range of from about 0.3 mil to about 3 mil.

22. The magnetic sheet assembly according to claim 1, wherein the pressure sensitive permanent adhesive has a thickness of about 0.5 mil.

23. The magnetic sheet assembly according to claim 1, wherein the pressure sensitive non-permanent adhesive has a thickness in a range of from about 0.3 mil to about 3 mil.

24. The magnetic sheet assembly according to claim 1, wherein the pressure sensitive non-permanent adhesive has a thickness of about 0.5 mil.

25. The magnetic sheet assembly according to claim 1, wherein the pressure sensitive non-permanent adhesive is capable of releasing clearly from a surface of the device.

26. A method of mounting, and removably adhering, a magnetic sheet assembly according to claim 1 to a surface of a device for magnetic separation, the method comprising the steps of:
   a) aligning the magnetic sheet assembly, having an exposed face comprising a non-permanent adhesive, with the surface of the device onto which it is desired to mount the magnetic sheet assembly; and
   b) pressing the aligned magnetic sheet assembly in placing the non-permanent adhesive face into adhesive contact with the surface of the device to removably adhere the magnetic sheet assembly to the surface of the device.

27. The method according to claim 26, wherein the method further comprises the step of removing the magnetic sheet assembly from the device by lifting and separating the magnetic sheet assembly from the device to which it was in adhesive contact, and wherein the non-permanent adhesive releases clearly from the surface of the device.

28. A method of mounting, and removably adhering, a magnetic sheet assembly according to claim 2 to a surface of a device for magnetic separation, the method comprising the steps of:
   a) removing the release liner from the magnetic sheet assembly so as to expose a face of the magnetic sheet assembly comprising the non-permanent adhesive;
   b) aligning the magnetic sheet assembly, having an exposed face comprising a non-permanent adhesive, with the surface of the device onto which it is desired to mount the magnetic sheet assembly; and
   c) pressing the aligned magnetic sheet assembly in placing the non-permanent adhesive face into adhesive contact with the surface of the device to removably adhere the magnetic sheet assembly to the surface of the device.

29. The method according to claim 28, wherein the method further comprises the step of removing the magnetic sheet assembly from the device by lifting and separating the magnetic sheet assembly from the device to which it was in adhesive contact, and wherein the non-permanent adhesive releases clearly from the surface of the device.

30. A magnetic sheet assembly for application to a device adapted for magnetic separation, wherein the magnetic sheet assembly comprises:
   at least one magnetic sheet comprising a plurality of poles of alternating polarities being generally arranged as a pattern selected from the group consisting of a plurality of parallel, spaced apart lines, and a grid pattern formed by a first plurality of poles of alternating polarities being generally arranged as a plurality of parallel, spaced apart lines which are perpendicular with respect to, and intersect, a second plurality of poles of alternating polarities being generally arranged as a plurality of parallel, spaced apart lines; and
   a double-sided pressure sensitive adhesive laminate comprised of a carrier sheet having applied on one side a permanent, pressure sensitive adhesive, and having applied on an opposite side a non-permanent, pressure sensitive adhesive, wherein the permanent, pressure sensitive adhesive is in adhesive contact with the at least one magnetic sheet in forming the magnetic sheet assembly.

31. The magnetic sheet assembly according to claim 30, further comprising a release liner which covers the non-permanent pressure sensitive adhesive.

32. The magnetic sheet assembly according to claim 30, wherein the at least one magnetic sheet has a surface magnetic field having a field strength in a range of from about 450 to about 1200 gauss.

33. A magnetic sheet assembly for application to a device adapted for magnetic separation, wherein the magnetic sheet assembly comprises:
   at least one magnetic sheet comprising a magnetization pattern comprising a uniform poling in a first poling over substantially all of a planar surface of the magnetic sheet, and a second poling of an opposite polarity to that of first poling, wherein the second poling comprises a plurality of spaced apart cylindrical regions which are parallel in relation to the first poling; and
   a double-sided pressure sensitive adhesive laminate comprised of a carrier sheet having applied on one side a permanent, pressure sensitive adhesive, and having applied on an opposite side a non-permanent, pressure sensitive adhesive, wherein the permanent, pressure sensitive adhesive is in adhesive contact with the at least one magnetic sheet in forming the magnetic sheet assembly.

34. The magnetic sheet assembly according to claim 33, further comprising a release liner which covers the non-permanent pressure sensitive adhesive.

35. The magnetic sheet assembly according to claim 33, wherein the at least one magnetic sheet has a surface magnetic field having a field strength in a range of from about 450 to about 1200 gauss.

36. A magnetic sheet, assembly for application to a device adapted for magnetic separation, wherein the magnetic sheet assembly comprises:
   at least one magnetic sheet comprising a plurality of magnets bonded to a material selected from the group consisting of a fibrous material, and a non-fibrous material; and
   a double-sided pressure sensitive adhesive laminate comprised of a carrier sheet having applied on one side a permanent, pressure sensitive adhesive having a first peel force, the double-sided pressure sensitive adhesive laminate having applied on an opposite side a non-permanent, pressure sensitive adhesive having a second peel force, wherein the first peel force is different than the second peel force.

37. The magnetic sheet assembly according to claim 35, further comprising a release liner which covers the non-permanent pressure sensitive adhesive.

38. The magnetic sheet assembly according to claim 37, wherein the plurality of magnets have a surface magnetic field having a field strength in a range of from about 450 to about 1200 gauss.

* * * * *